(12) United States Patent
McReynolds et al.

(10) Patent No.: US 9,650,667 B2
(45) Date of Patent: May 16, 2017

(54) METHOD FOR REDUCING ADAPTER-DIMER FORMATION

(71) Applicant: New England Biolabs, Inc., Ipswich, MA (US)

(72) Inventors: Larry A. McReynolds, Beverly, MA (US); Daniela Munafo, South Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 193 days.

(21) Appl. No.: 14/508,508

(22) Filed: Oct. 7, 2014

(65) Prior Publication Data

US 2015/0072870 A1    Mar. 12, 2015

Related U.S. Application Data

(63) Continuation of application No. 13/383,466, filed as application No. PCT/US2011/049972 on Aug. 31, 2011, now Pat. No. 8,883,421.

(60) Provisional application No. 61/381,801, filed on Sep. 10, 2010.

(51) Int. Cl.
*C12Q 1/68* (2006.01)
*C12N 15/10* (2006.01)

(52) U.S. Cl.
CPC ....... *C12Q 1/6855* (2013.01); *C12N 15/1065* (2013.01); *C12N 15/1096* (2013.01); *C12Q 1/6832* (2013.01); *C12Q 1/6869* (2013.01)

(58) Field of Classification Search
CPC ............ C12N 15/1065; C12N 15/1096; C12Q 1/6832; C12Q 1/6855; C12Q 1/6869
See application file for complete search history.

(56) References Cited

U.S. PATENT DOCUMENTS

2011/0104785 A1    5/2011    Vaidyanathan et al.

FOREIGN PATENT DOCUMENTS

WO    WO 2006/110161 A2    10/2006
WO    WO 2008/097957 A2    8/2008

OTHER PUBLICATIONS

International Sea, WO, Jan. 3, 2012, PCT/US2011/049972.
Pease, Nature Methods, 8:iii-iv (2011).
Kawano, et al, Biotechniquest 49(4):751-755 (2010).
Lau, et al, Science 294:858-862 (2001).
Sambrook, et al, Molecular Cloning: A Laboratory Manual, 2nd ed, Cold Spring Harbor Laboratory Press (1989).
Ho, et al, Journal of Virological Methods, 136:217-223 (2006).
Lu, et al, Methods, 43:110-117 (2007).
Tschudi, et al, Methods, 30:304-312 (2003).

*Primary Examiner* — Cynthia B Wilder
(74) *Attorney, Agent, or Firm* — New England Biolabs, Inc; Harriet M. Strimpel

(57) ABSTRACT

Methods are provided for ligating a 3' adapter and a 5' adapter to a target polynucleotide so as to avoid adapter dimer formation. Embodiments of the methods include adding a blocking oligonucleotide after the first ligation in which a 3' adapter is ligated to the target polynucleotide so that the blocking oligonucleotide is capable of hybridizing to excess 3' adapter and the ligated 3' adapter. Subsequently, a 5' adapter is ligated to the target polynucleotide thus avoiding adapter dimer formation.

17 Claims, 4 Drawing Sheets

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
cgccttggcc gtacagcag                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
ctgctgtacg gccaaggcg                                              19

<210> SEQ ID NO 3
<211> LENGTH: 46
<212> TYPE: RNA
<213> ORGANISM: Artificial Sequence
<220> FEATURE:
<223> OTHER INFORMATION: Synthetic Construct
```

```
<400> SEQUENCE: 3
rcrcrurcru rcrurarurg rgrgrcrarg rurcrgrgru rgraru          46
```

METHOD FOR REDUCING ADAPTER-DIMER FORMATION

CROSS REFERENCE

This application is a continuation of U.S. patent application Ser. No. 13/383,466 filed Jan. 11, 2012, which is a §371 application of international application number PCT/US2011/049972 filed Aug. 31, 2011, herein incorporated by reference. This application also claims priority from U.S. provisional application Ser. No. 61/381,801 filed Sep. 10, 2010, herein incorporated by reference.

BACKGROUND OF THE INVENTION

Methods for characterizing RNAs generally require the attachment by ligation of adapters of known sequence to the 3' end and to the 5' end of a target RNA. The ligation reactions are preferably performed in sequence and utilize an excess of the adapters. An undesirable consequence of the ligation reaction is the formation of dimers consisting of the 3' adapter and the 5' adapter which in subsequent reactions involving cloning or amplification give rise to significant background.

Degradation of the excess 3' adapters has been achieved enzymatically. For example, Pease, *Nature Methods*, 8: iii-iv (2011), and Vaidyanathan, et al., United States Patent Application US 2011/0104785 A1, describe the use of nucleases after individual ligation steps. However, the enzyme must be inactivated prior to addition of a 5' adapter for ligation to avoid its degradation during subsequent ligation steps.

Another approach relies on a spanning oligonucleotide which is complementary to the junction of the adapter dimer. The spanning oligonucleotide is used to prevent the adapter dimer from being copied into ssDNA by reverse transcriptase (Kawano et al., *Biotechniques* 49(4): 751-755 (2010)). Unfortunately, design constraints are imposed on the sequence of the spanning oligonucleotide. The spanning oligonucleotide must block cDNA synthesis of the adapter dimer but not block cDNA synthesis of the ligated target RNA. Moreover, formation of the dimer is not blocked. Instead, the method prevents the dimer from being copied into a second strand. An adverse consequence of using a spanning oligonucleotide is that a majority of the 5' adapter and the ligase in the second ligation are used for formation of the oligonucleotide dimer, not for ligation to the target RNA which reduces the yield of ligated target RNA.

A standard approach to reducing high background is described by Lau et al., *Science* 294:858-862 (2001), who used gel purification of the first ligation product to remove excess 3' adapter that was not ligated to the RNA. However, this approach preferentially uses reduced amounts of the adapters to reduce dimer formation and this in turn reduces the yield of the desired product for cloning or sequencing.

SUMMARY OF THE INVENTION

A method is provided for ligating a 3' adapter and a 5' adapter to a single strand polynucleotide so as to avoid adapter dimer formation. The method includes (a) performing a first ligation between a 3' end adapter and a single strand polynucleotide to form a first ligation product; (b) adding a blocking oligonucleotide for hybridizing to the 3' adapter so that the 3' adapter is no longer capable of being ligated to a 5' adapter; and (c) ligating the first ligation product to a 5' adapter in the absence of adapter dimer formation. In an embodiment of the invention, the 3' adapter may be a DNA, the 5' adapter may be RNA, and the blocking oligonucleotide may be a DNA capable of acting a primer for reverse transcription or amplification.

In an additional embodiment of the invention, the blocking oligonucleotide can be used in protocols that are independent of ligation to the 5' end of the RNA. These protocols include ligation of a 3' adapter to the target RNA, synthesis of a cDNA using the blocking oligo as a primer, followed by ligation of a second adapter to the 3' end of the cDNA. The presence of the blocking oligo prevents the first 3' adapter from ligating to the end of the cDNA but allows ligation of the second adapter.

The method described herein may be used for any application which utilizes a cDNA library or requires an amplification step including cloning, sequencing and quantification of a target polynucleotide. The target polynucleotide may be obtained from a cell or from a polynucleotide library.

In another embodiment of the invention, a kit is contemplated which includes a 3' adapter, a 5' adapter, a blocking oligonucleotide and instructions for their sequential use.

In another embodiment, the methods described above may additionally utilize a 3' adapter containing a barcode for identifying the target RNA. Moreover, the barcode may be capable of distinguishing a first target RNA or a first set of target RNAs from a second RNA or a second set of target RNAs. Additionally, the barcode may be capable of performing at least one of cloning, quantifying or sequencing the first target RNA or the first set of RNAs and the second RNA or second set of RNAs. The blocking oligo can be designed to hybridized to 3' adapters that contains a barcode.

BRIEF DESCRIPTION OF THE FIGURES

FIG. 1A shows a target RNA on the left and a 3'-DNA adapter on the right which is pre-adenylated (App) at the 5' end and blocked at the 3' end (X).

FIG. 1B shows the products of ligation of the target RNA to the 3' DNA adapter and excess 3' DNA adapter.

FIG. 1C shows the annealing of a blocking oligonucleotide to both the ligated and unligated 3' DNA adapter to form a double stranded 3' adapter.

FIG. 1D shows the products of ligation of a 5' RNA adapter to the 5' end of the target RNA oligonucleotide ligated to the 3' DNA adapter that is hybridized to a blocking DNA oligonucleotide. Excess 3' DNA adapter is also hybridized to the blocking oligonucleotide to form a double stranded molecule and is this unable to become ligated to excess 5' RNA adapter as shown.

FIG. 1E shows the extension by reverse transcription of the blocking oligonucleotide where the blocking oligonucleotide is hybridized to the 3' adapter. The extension reaction forms a complementary DNA to that of the target RNA.

FIG. 2A shows a 10% urea denaturing polyacrylamide gel where:

Lane 1 contains the 3' DNA adapter monomer prior to the first ligation step;

Lane 2 contains the target RNA prior to the first ligation step;

Lane 3 contains the product of the 3' ligation step. The heavy band is the RNA ligated to the 3' DNA adapter;

Lane 4 contains the 5' RNA adapter only;

Lane 5 shows the product of the 5' ligation step which is a 3' 5' ligated RNA (RNA/DNA chimera). The presence of excess 3' adapter monomers can be observed. The blocking oligonucleotide runs at the same position as the 3' adapter. Significantly, no 3' adapter dimers or 3'/5' adapter dimers are observed which would be expected in the 40-50 nt region of the gel in the absence of the blocking oligonucleotide;

Lane 6 shows the first strand DNA that is the product of reverse transcription (cDNA) and the 3'5' ligated RNA template;

Lane 7 contains makers.

Figure 1A:
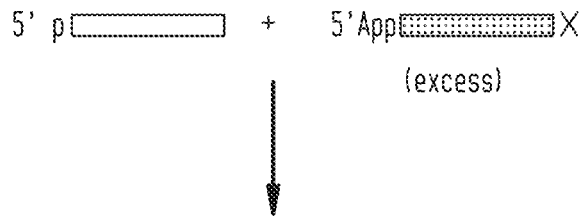
FIGS. 1A-E show a cartoon of a series of reactions that convert a target polynucleotide into a cDNA wherein the target polynucleotide is ligated to adapters for primer dependent amplification and sequencing. This is referred to in the Examples as the NEB method.
Figure 1B:
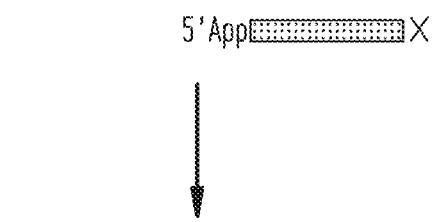
Figure 1C:
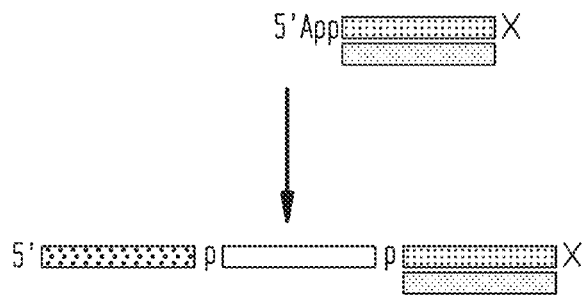
Figure 1D:
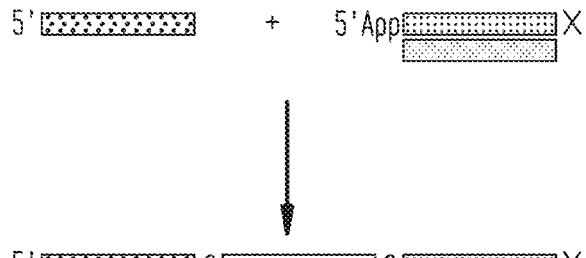
Figure 1E:
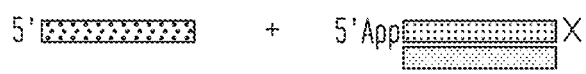
Figure 2A:
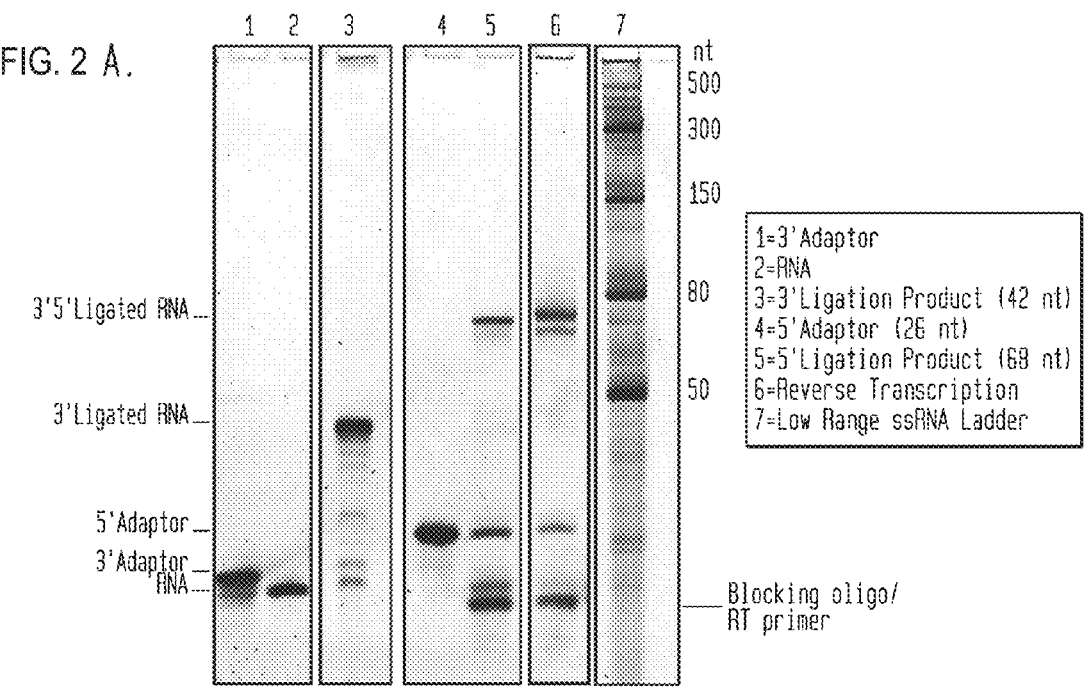
FIGS. 2A and 2B show that the blocking oligonucleotide is effective in preventing dimer formation and does not interfere with RNA ligation of the 5' adapter to an RNA oligonucleotide nor with reverse transcription using synthetic target RNA, a 3' DNA adapter, a 5' RNA adapter and suitable primers analyzed on 10% urea denaturing polyacrylamide gel.
Figure 2B:
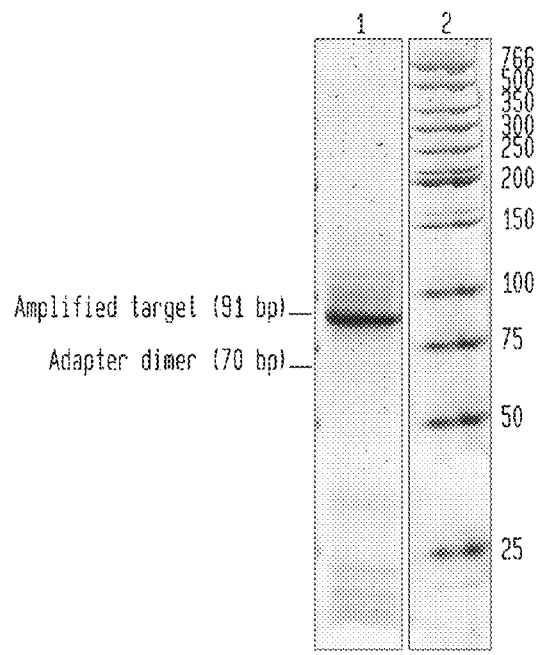

FIG. 2B shows a 6% native polyacrylamide gel. Lane 1 shows a single band corresponding to the amplified product (91 bp) and no band at the position (70 bp) corresponding to an amplified adapter dimer. Lane 2 is a MW marker.

Figure 3:
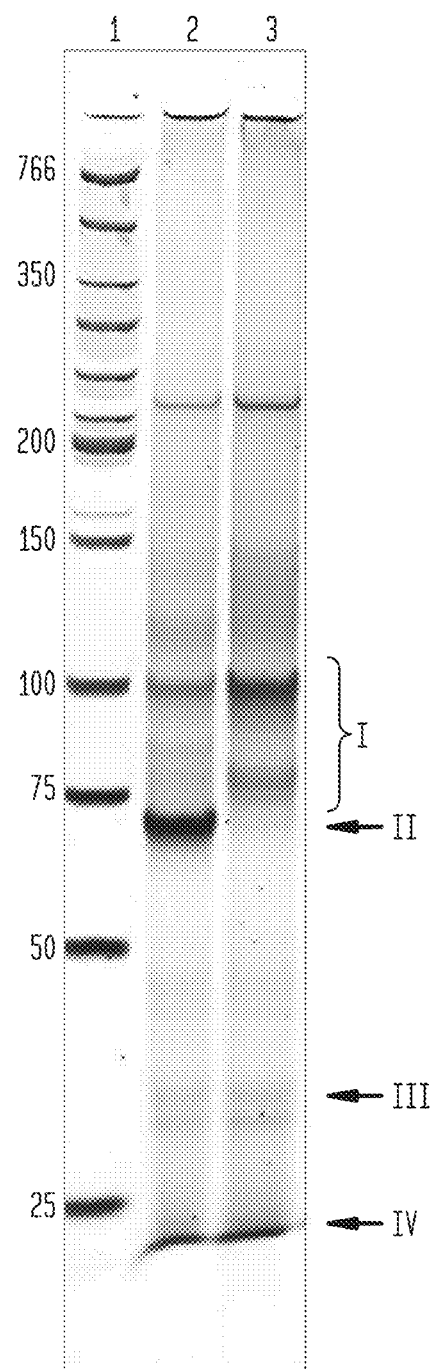

FIG. 3 shows a native 6% polyacrylamide gel where lane 1 contains a low molecular weight DNA ladder, lane 2 shows amplified DNA derived from rat testis RNA after adapter ligation using standard methods and reverse transcription and amplification (lane 2). Lane 3 shows the results obtained using blocking oligonucleotides as described in the method of FIGS. 1A-E. The bands at the position indicated by (II) represent adapter-dimers (lane 2). The bands within the region indicated by (I) represent the adapter-ligated cDNA library (lane 3). (III) and (IV) correspond to PCR primers.

Figure 4A:
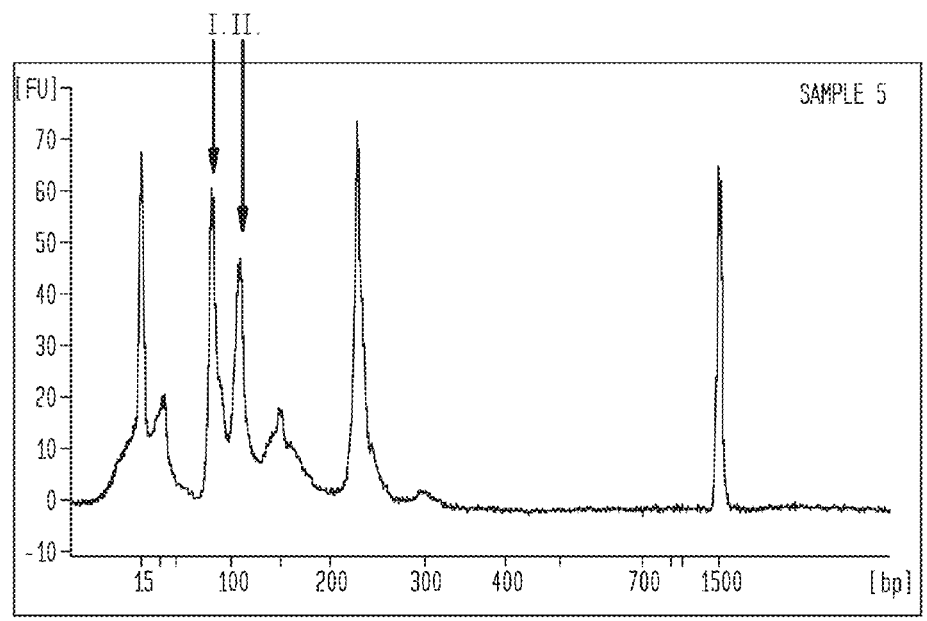
Figure 4B:
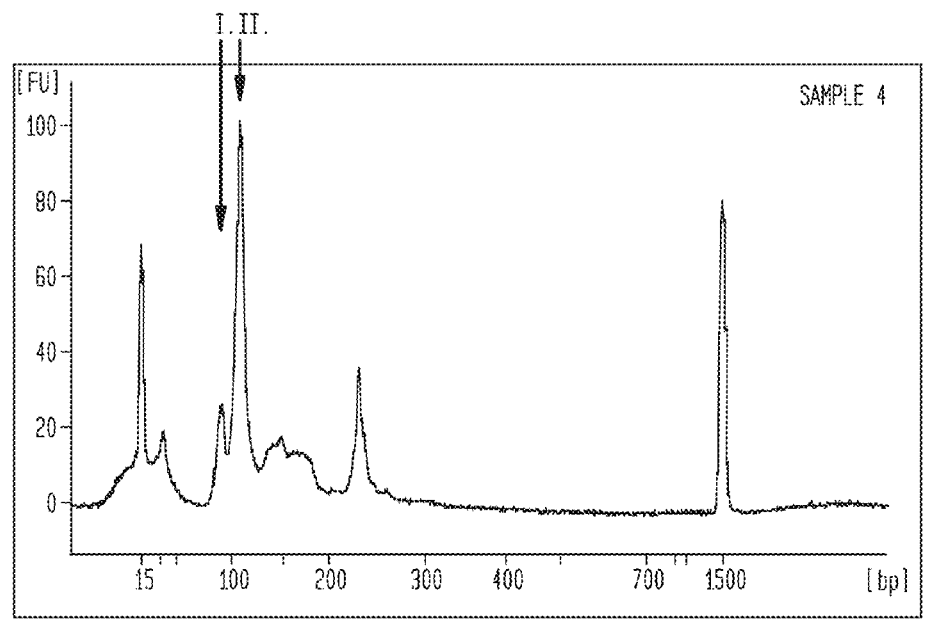

FIGS. 4A and 4B show electropherograms produced by a 2100 Bioanalyzer (Agilent, Santa Clara, Calif.) of rat testis total RNA cDNA libraries prepared by a standard method and a method of the present invention.

Peak (I) represents adapter-dimer contamination. Peak (II) represents the cDNA library.

FIG. 4A shows results from a standard prior art method.

FIG. 4B shows the results from the method outlined in FIGS. 1A-E.

DETAILED DESCRIPTION OF THE EMBODIMENTS

A solution to the problem of adapter dimerization is provided herein for methods that require a plurality of ligation steps involving a single strand polynucleotide and 3' and 5' adapters for purposes related to at least one of cloning, characterization and quantification of the polynucleotide.

In an embodiment of the method, a blocking oligonucleotide is introduced into the reaction mixture after a first ligation step and before a second ligation step. Typically, the first ligation step involves ligation of the polynucleotide at its 3' end to a 3' adapter where the 3' adapter is in excess.

The second ligation step is the ligation of a 5' adapter to the 5' end of the polynucleotide. The blocking oligonucleotide hybridizes to an excess of the 3' adapter from the first ligation thereby preventing it from forming a dimer with the 5' adapter introduced into the second ligation reaction. An advantage of this approach is that the blocking oligonucleotide may additionally serve as a primer for subsequent reactions such as reverse transcription. The figures and examples show that the presence of the blocking primer after the first ligation step does not adversely affect subsequent ligation steps while blocking dimerization of the adapters.

This method finds utility for those reactions that require a ligation step in which a 3' adapter is ligated to a target polynucleotide. The subsequent ligations steps may involve for example ligating a 5' adapter to the 5' end of the target polynucleotide. Optionally, an additional oligonucleotide may be ligated to the 5' end of the 5' adapter.

Examples of uses of blocking oligonucleotides include reducing background, which is exacerbated during amplification of a reverse transcript of an RNA, for sequencing reactions (for example Next Gen sequencing or Sanger sequencing), quantification and/or cloning or other uses known in the art.

Certain terms used to describe embodiments of the invention are described below in further detail.

"Polynucleotide", as used herein, refers to a single stranded RNA, a DNA or a chimeric molecule consisting of RNA and DNA. Where the polynucleotide is a target molecule, it may be a single species derived from nature or may be synthetic or may be part of a library of oligonucleotides where the members of the library are derived from a cell or genome or other source such that the members of the library vary in their sequences.

Where the target polynucleotides is an RNA, the RNA may include micro RNAs (miRNAs), PIWI associated RNAs (piRNAs), short interfering RNAs (siRNAs), endogenous short interfering RNAs (esiRNAs) and short hairpin RNAs (shRNAs). Messenger RNA, fragments of mRNA, viral RNA and structural RNAs like rRNA, tRNA and 5S RNA can all be ligated and amplified by this approach. There are no size or sequence requirements for the polynucleotide. However, the polynucleotide must have a free 3' OH to allow its' ligation to a 3' adapter.

"Adapter", as used herein, refers to a single strand polynucleotide. A 3' adapter refers to an adapter which is capable of being ligated to a target polynucleotide at the 3' end of the RNA. The 3' adapter may include an adenylated 5' terminus (5' App) and have a blocking group (X) on the 3' end to prevent ligation at the 3' end. A blocking group refers to any modification which prevents the 3' terminus of the adapter from participating in a ligation reaction. Examples of blocking groups include amino groups, inverted 3'-3' nucleotide linkages and dideoxy-nucleotides.

The 5' adapter refers to an adapter that is capable of being ligated to the 5' end of the RNA. In certain embodiments the 5' adapter is RNA and the 3' adapter is DNA. Individual adapters are generally at least 10 or more nucleotides and preferably less than 100 nucleotides or 50 nucleotides or 30 nucleotides in length. The adapters may contain primer binding sites from which primer dependent amplification of adapter-flanked target molecules can proceed. Additionally the adapters may contain modifications or labels such as Biotin or other label known in the art which enhance separation or identification of adapter-target constructs.

"Adapter dimer", as used herein, refers to the product of ligation between the 5' App of the 3' adapter and the 3' end of the 5' adapter.

"Blocking oligonucleotide", as used herein, refers to a polynucleotide that may be synthetic and is capable of hybridizing to the 3' adapter and to the first ligation product containing the 3' adapter. The size of the blocking oligonucleotide may be less or greater than the size of the 3' adapter although it must block the 5' App from ligating to a 3' end of a 5' adapter and must not itself be readily capable of ligation to the 5' end of the target polynucleotide. Additional desirable features include: a lack of a phosphate at the 5' end of the blocking oligonucleotide; and a blunt end formed by the 5' end of the adenylated linker annealed to the 3' end of the blocking oligonucleotide.

The blocking oligonucleotide may be 60%, 70%, 80%, 90%, 95% or 99% complementary in sequence to the 3' adapter, the extent of sequence homology being inversely proportional to the stringency of the hybridization conditions. When the blocking oligonucleotide hybridizes to part or all of the 3' adapter it forms a substantially stable double-stranded structure that does not self-ligate or ligate to anything else as determined by standard detection methods. The number of hybridizing base pairs required to form a stable double-stranded structure is dependent on factors such as the base composition of the region, the salt concentration of the solution and the temperature of the solution (Sambrook et al., *Molecular Cloning: A Laboratory Manual*, 2$^{nd}$ ed, Cold Spring Harbor Laboratory Press (1989)).

Moreover, in one embodiment, a blocking oligonucleotide may contain a 3'-hydroxyl group from which an extension reaction can proceed. Examples of extension reactions include polymerase chain reaction (PCR) or reverse-transcription PCR (RT-PCR). Hence, the blocking oligonucleotide may possess the established required features of a primer.

"Hybridizing", as used herein, refers to those conditions described in, for example, Sambrook et al., that cause a single strand polynucleotide to anneal to another single stranded polynucleotide having a substantially complementary sequence.

"Ligating", as used herein, refers to joining of separate single stranded polynucleotides to each other to form a single molecule. This is commonly but not exclusively achieved by means of a ligase. An RNA ligase can readily ligate a single strand DNA to a single strand RNA at the 3' end of the RNA. An RNA ligase can also readily ligate a 5' end of an RNA to a 3' end of an RNA. The ligation reactions described herein are generally achieved by means of a ligase such as available commercially and described in the New England Biolabs, Inc. catalog. Ligases include ATP-requiring RNA ligases such as a T4 RNA ligase 1 and T4 RNA ligase 2 truncated and mutants of T4 RNA ligase 2 as described in the examples.

All references cited herein, as well as U.S. Provisional Application No. 61/381,801 filed Sep. 10, 2010, are herein incorporated by reference.

EXAMPLES

Example 1

Making a cDNA Library from Total RNA Using the NEB Method

Step 1: 3' Adapter Ligation.

Using input total RNA or isolated small RNA from total RNA, the following reaction mixture was prepared:

| | |
|---|---|
| Input RNA (1-10 µg) | 6 µl |
| 3' Adapter (10 µM) | 1 µl |
| 5'-rAppCGCCTTGGCCGTACAGCAG-NH2-3' | (SEQ ID NO: 1) |

For example, Human brain total RNA (5 ug) can be used in the analysis. The reaction mixture was heated at 70° C. for 2 minutes, then snap cooled on ice. The following reagents were additionally added to a final volume of 20 µl:

| | |
|---|---|
| 3' Ligation Reaction Buffer | 10 µl |
| Containing: | |
| 100 mM Tris-HCl (pH 7.5) | |
| 20 mM MgCl2 | |
| 2 mM DTT | |
| 25% W/V Polyethylene Glycol 8,000 MW | |
| 3' Ligase Enzyme Mix | 3 µl |
| Containing: | |
| T4 RNA Ligase 2 truncated (133,000 U/ml) | |
| Murine RNase Inhibitor (13,000 U/ml) | |

The reaction mixture was then incubated for 1 hour at 25° C. to form a 3' ligation product.

Step 2: Addition of a Blocking Oligonucleotide to the 3' Ligation Product.

The following was added to a final volume of 25.5 ul

| | |
|---|---|
| Nuclease-free water | 4.5 µl |
| Blocking oligonucleotide (50 µM) | 1 µl |
| 5'-CTGCTGTACGGCCAAGGCG-3' | (SEQ ID NO: 2) |

The reaction mixture was heated for 2 minutes at 70° C., transferred to 37° C. for 15 minutes, and then cooled slowly to room temperature for 15 minutes to permit annealing of the blocking oligonucleotide.

Step 3: 5' Adapter Ligation

The following components were added to 25.5 µl of reaction mixture from step 2 to a final volume of 30 µl:

| | |
|---|---|
| 5' Adapter (20 µM) | 1 µl |
| 5'-rCrCrUrCrUrCrUrArUrGrGrCrArGrUrCrGrUrGrArU-3' | |
| (SEQ ID NO: 3) | |
| 5' Ligation Reaction Buffer | 1 µl |
| Containing: | |
| 500 mM Tris-HCl (pH 7.5) | |
| 100 mM MgCl2 | |
| 10 mM DTT | |
| 30 mM ATP | |
| 5' Ligase Enzyme Mix | 2.5 µl |
| Containing: | |
| T4 RNA Ligase 1 (12,000 U/ml) | |
| Murine RNase Inhibitor (16,000 U/ml) | |

The reaction mixture was incubated for 1 hour at 25° C. in a thermal cycler.

Step 4: Reverse Transcription.

11 µl of the 3'5' ligation product was added as a template for reverse transcriptase to the following components in a final volume of 19 µl:

| | |
|---|---|
| Deoxynucleotide solution mix (10 mM) | 1 µl |
| 5X First Strand Buffer | 4 µl |
| Containing: | |
| 250 mM Tris-HCl (pH 8.3) | |
| 375 mM KCl | |
| 15 mM MgCl2 | |
| 0.1M DTT | 2 µl |
| Murine RNase Inhibitor (40,000 U/ml) | 1 µl |

The reaction mixture was heated for 2 minutes at 42° C. Then 1 µl SuperScript II® Reverse Transcriptase (200 U/µl) (Life Technologies, Carlsbad, Calif.) was added and the reaction mixture was incubated for 1 hour at 42° C.

Step 5: PCR Amplification

20 µl reverse transcriptase reaction mixture from step 4 was combined with the following components to make a final volume of 50 µl:

| | |
|---|---|
| LongAmp ® Taq 2X Master Mix (New England Biolabs, Inc., Ipswich, MA) | 25 µl |
| Forward Primer (10 µM) | 2.5 µl |
| Reverse Primer (10 µM) | 2.5 µl |

The reaction mixture was then subjected to the following PCR conditions:

TABLE 1

PCR conditions

| Cycle Step | Temperature | Time (Seconds) | Cycles |
|---|---|---|---|
| Initial Denaturation | 94° C. | 10 | 1 |
| Denaturation | 94° C. | 10 | 12-15 |
| Annealing | 60° C. | 30 | 12-15 |
| Extension | 65° C. | 15 | 12-15 |
| Final Extension | 65° C. | 600 | 1 |
| Hold | 4° C. | ∞ | 1 |

Example 2

Making a cDNA Library from Total RNA Using the Standard Method (NEB Method without the Use of a Blocking Oligonucleotide)

Step 1: 3' Adapter Ligation
In a 0.2 ml PCR tube mix the following components:

| | |
|---|---|
| Human Brain total RNA (5 µg) | 6 µl |
| 3' Adapter (10 µM) (SEQ ID NO: 1) | 1 µl |

In a thermo cycler, heat sample at 70° C. for 2 min; then snap cooled on ice.
Add the following reagents to a final volume of 20 µl:

| | |
|---|---|
| 3' Ligation Reaction Buffer<br>Containing:<br>100 mM Tris-HCl (pH 7.5)<br>20 mM MgCl2<br>2 mM DTT<br>25% W/V Polyethylene Glycol 8,000 MW | 10 µl |
| 3' Ligase Enzyme Mix<br>Containing:<br>T4 RNA Ligase 2 truncated (133,000 U/ml)<br>Murine RNase Inhibitor (13,000 U/ml) | 3 µl |

Incubate reaction in a thermo cycler for 1 hour at 25° C.
Step 2: 5' Adapter Ligation
Add the following components to the 20 µl reaction mixture from step 1 to a final volume of 30 µl:

| | |
|---|---|
| 5' Adapter (20 µM) (SEQ ID NO: 3) | 1 µl |
| 5' Ligation Reaction Buffer<br>Containing:<br>500 mM Tris-HCl (pH 7.5)<br>100 mM MgCl2<br>10 mM DTT<br>30 mM ATP | 1 µl |
| 5' Ligase Enzyme Mix<br>Containing:<br>T4 RNA Ligase 1 (12,000 U/ml)<br>Murine RNase Inhibitor (16,000 U/ml)<br>Nuclease-free water 5.5 µl | 2.5 µl |

Incubate reaction for 1 hour at 25° C. in a thermal cycler.
Step 3: Reverse Transcription
In a clean 0.2 ml PCR tube mix the following components:

| | |
|---|---|
| 3'5' ligation product (from step 2) | 10 µl |
| Reverse Transcriptase primer (50 µM) | 1 µl |

Heat sample at 70° C. for 5 minutes, then transfer to ice.
Add the following reagents:

| | |
|---|---|
| Deoxynucleotide solution mix (10 mM) | 1 µl |
| 5X First Strand Buffer<br>Containing:<br>250 mM Tris-HCl (pH 8.3)<br>375 mM KCl<br>15 mM MgCl2 | 4 µl |
| 0.1M DTT | 2 µl |
| Murine RNase Inhibitor (40,000 U/ml) | 1 µl |

Incubate the reaction mixture at 42 C for 2 minutes, then add 1 µl SuperScript II® Reverse Transcriptase (200 U/µl) (Life Technologies, Carlsbad, Calif.) and incubate for 1 hour at 42° C.
Step 4: PCR Amplification

| | |
|---|---|
| Reverse transcriptase reaction from step 3 | 20 µl |
| LongAmp ® Taq 2X Master Mix | 25 µl |
| Forward Primer (10 µM) | 2.5 µl |
| Reverse Primer (10 µM) | 2.5 µl |

The reaction mixture was then subjected to the following PCR conditions:

TABLE 2

PCR conditions

| Cycle Step | Temperature | Time (Seconds) | Cycles |
|---|---|---|---|
| Initial Denaturation | 94° C. | 10 | 1 |
| Denaturation | 94° C. | 10 | 12 |
| Annealing | 60° C. | 30 | 12 |
| Extension | 65° C. | 15 | 12 |
| Final Extension | 65° C. | 600 | 1 |
| Hold | 4° C. | ∞ | 1 |

Example 3

Method for Increasing the Yield of the Library

Small RNA libraries were made from human brain total RNA (5 µg) using either the NEB method (the "NEB method" as used throughout is a present embodiment of the invention that relies on use of blocking oligonucleotides as shown in FIGS. 1A-E) or standard ligation protocols ("standard" protocol refers to the same protocol as used in the NEB method absent the use of a blocking oligonucleotide). Standard libraries were made using three times lower adapter concentration compared with the amount of adapter generally recommended and compared to the amount used in the NEB method so as to reduce background. NEB libraries yielded 114 ng (2.28%) while standard library yielded 14.6 ng (0.29%) after 12 cycles of PCR amplification. This data showed that NEB libraries yielded about ten times more amplicon (ng) than the standard protocol. The NEB method allowed the use of high levels of 3' adapter because of the elimination of background resulting from dimer formation (see for example FIG. 3).

Example 4

Deep Sequencing Data Analysis of Small RNA Libraries

Human brain small RNA libraries were made from total RNA (5 µg) using standard ligation protocols or NEB method. Libraries were deep sequenced on SOLiD™ 4 sequencer (Life Technology, Carlsbad, Calif.). Both methods generate approximately 100 million of 35 bp length reads. The reads were trimmed removing the SOLiD™ miRNA reverse primer (CTGCTGTACGGCCAAGGCG) (SEQ ID NO: 2) on the minus strand. Reads that did not contain primer sequence were discarded. After primer trimming, the reads were filtered based on length. Reads shorter than 15 nucleotides or longer than 55 nucleotides were discarded after trimming and filtering on length. The NEB method recovered 70,414,785 (67.45%) reads compare with standard methods that recovered 34,956,638 (37.84%) reads. Trimmed and filtered reads were mapped against the miRbase data base (miRbase version 16). Approximately thirty millions reads (30% of total reads) were generated using the NEB method, and sixteen millions reads (18% of total reads) were generated using the standard method mapped against MIRbase, respectively. This data shows that the NEB method generates a higher number of reads that contain full length RNA target. This method can provide better resolution of pooled samples with reduced background.

TABLE 3

Improved resolution of pooled samples

| | Standard | NEB |
|---|---|---|
| Number of Reads | 92390612 | 104393760 |
| Number of Reads after trim | 34956638 | 70414785 |
| Percent trim | 37.84% | 67.45% |
| Average length after trim | 22.1 | 21.6 |
| Annotated | 16,415,714 | 30,350,083 |

Example 5

Multiplexing

The method described in Example 1 can be applied to multiple target RNAs as follows:

Individual or sets of RNAs can be placed into different reaction vessels and a different 3' adapter or a plurality of 3' adapters can be added to each reaction vessel where the 3' adapter contains a barcode located at one end or within the adapter such that when the 3' adapter is ligated to the target RNA, an address for that target RNA is provided. It is then possible to combine all the 3' adapter-target RNA ligation products into a single reaction vessel, add a single oligonucleotide blocker or multiple oligonucleotide blockers as desired and then ligate a 5' adapter and continue as described in Example 1 to perform reverse transcription and amplification for cloning, quantification, or sequencing purposes.

What is claimed is:

1. A kit comprising:
    (a) a 3' adapter oligonucleotide having a non-natural 3' end that prevents ligation of the 3' end of the 3' adapter oligonucleotide to another polynucleotide;
    (b) a blocking oligonucleotide that has a 3' hydroxyl group and at least 10 nucleotides of complementary to the 3' adapter, wherein the blocking oligonucleotide:
        hybridizes to the 3' adaptor oligonucleotide to produce a duplex having a blunt end comprising the 3' hydroxyl group of the blocking oligonucleotide; and
        primes cDNA synthesis of an RNA polynucleotide when the 3' adaptor oligonucleotide is ligated to the 3' end of the RNA polynucleotide; and
    (c) a buffer comprising a non-naturally occurring buffering agent.

2. A kit according to claim 1, further comprising a first ligase.

3. A kit according to claim 1 further comprising a second ligase.

4. A kit according to claim 3, wherein the second ligase is a T4 mutant ligase.

5. A kit according to claim 1, wherein the blocking oligonucleotide is a DNA.

6. A kit according to claim 1 further comprising a 5' adapter.

7. A kit according to claim 1, further comprising a reverse transcriptase.

8. A kit according to claim 1, wherein the 3' adapter has a length of 10-50 nucleotides.

9. A kit according to claim 1, wherein the 3' adapter is pre-adenylated.

10. A reaction mixture, comprising:
    (a) a 3' adapter oligonucleotide having a non-natural 3' end that prevents ligation of the 3' end of the 3' adapter oligonucleotide to another polynucleotide ;
    (b) a buffer comprising a non-naturally occurring buffering agent; and
    (c) a polynucleotide; and
    (d) a blocking oligonucleotide has a 3' hydroxyl group and at least 10 base pairs of complementary to the 3' adapter oligonucleotide, wherein:
        i. some of the 3' adapter oligonucleotide is ligated to the 3' end of the polynucleotide and some of the 3' adapter oligonucleotide is not ligated to the 3' end of the polynucleotide; and
        ii. the blocking oligonucleotide is hybridized to at least the 3' adapter oligonucleotide that is not ligated to the 3' end of the polynucleotide to produce a duplex having a blunt end comprising the 3' hydroxyl group of the blocking oligonucleotide.

11. A reaction mixture according to claim 10, wherein the polynucleotide is an RNA and the 3' adapter is a DNA.

12. A reaction mixture according to claim 10, further comprising a 5' adapter ligated to the polynucleotide.

13. A reaction mixture according to claim 10, further comprising a reverse transcriptase.

14. A reaction mixture according to claim 10, wherein the polynucleotide is a member of a polynucleotide library wherein the polynucleotides in the library are ligated to 3' adapters.

15. A reaction mixture according to claim 10, wherein the 3' adapters contain a barcode.

16. A reaction mixture comprising:
    (a) a 3' adapter oligonucleotide having a non-natural 3' end that prevents ligation of the 3' end of the 3' adapter oligonucleotide to another polynucleotide;
    (b) a buffer comprising a non-naturally occurring buffering agent; and
    (c) a polynucleotide; and
    (d) a blocking oligonucleotide has a 3' hydroxyl group and at least 10 nucleotides of complementary to the 3' adapter oligonucleotide, wherein:
        i. some of the 3' adapter oligonucleotide is ligated to the 3' end of the polynucleotide and some of the 3' adapter oligonucleotide is not ligated to the 3' end of the polynucleotide; and
        ii. the blocking oligonucleotide is hybridized to at least the 3' adapter oligonucleotide that is not ligated to the 3' end of the polynucleotide,
        wherein different polynucleotides ligated to a 3' adapter are pooled from multiple samples and the blocking oligonucleotide is hybridized to excess 3' adapter oligonucleotide.

17. A reaction mixture according to claim 10, wherein the polynucleotide is a member of a library of polynucleotides.

* * * * *